(12) United States Patent
Maury et al.

(10) Patent No.: US 10,467,746 B2
(45) Date of Patent: Nov. 5, 2019

(54) METHOD FOR PRODUCING TEETH SURFACE FROM X-RAY SCAN OF A NEGATIVE IMPRESSION

(71) Applicant: Carestream Dental Technology Topco Limited, London (GB)

(72) Inventors: Colombe Maury, Marne la Vallee (FR); Xavier Ripoche, Marne la Vallee (FR); Vincent Loustauneau, Fontenay sous Bois (FR); Sylvie M. Bothorel, Paris (FR); Jean-Marc Inglese, Bussy Saint Georges (FR); Edward R. Shellard, Atlanta, GA (US)

(73) Assignee: CARESTREAM DENTAL TECHNOLOGY TOPCO LIMITED, London (GB)

( * ) Notice: Subject to any disclaimer, the term of this patent is extended or adjusted under 35 U.S.C. 154(b) by 564 days.

(21) Appl. No.: 14/765,351

(22) PCT Filed: Mar. 10, 2014

(86) PCT No.: PCT/US2014/022345
§ 371 (c)(1),
(2) Date: Aug. 3, 2015

(87) PCT Pub. No.: WO2014/164405
PCT Pub. Date: Oct. 9, 2014

(65) Prior Publication Data
US 2016/0148370 A1 May 26, 2016

Related U.S. Application Data

(60) Provisional application No. 61/775,942, filed on Mar. 11, 2013, provisional application No. 61/775,949, filed on Mar. 11, 2013.

(51) Int. Cl.
*G06T 11/00* (2006.01)
*G06T 17/00* (2006.01)
(Continued)

(52) U.S. Cl.
CPC .......... *G06T 7/0012* (2013.01); *A61C 9/0006* (2013.01); *G06K 9/4604* (2013.01);
(Continued)

(58) Field of Classification Search
USPC ......................................... 348/77
See application file for complete search history.

(56) References Cited

U.S. PATENT DOCUMENTS

| 5,605,459 A | * | 2/1997 | Kuroda | ................. | A61C 7/002 433/214 |
| 6,217,334 B1 | * | 4/2001 | Hultgren | .............. | A61C 9/0006 433/215 |

(Continued)

FOREIGN PATENT DOCUMENTS

| CA | 2 346 256 A1 | 4/2000 |
| EP | 1 119 312 B1 | 6/2008 |

(Continued)

OTHER PUBLICATIONS

International Search Report dated Sep. 12, 2014 for International Application No. PCT/US2014/022345, 3 pages.
(Continued)

*Primary Examiner* — Deirdre L Beasley (57) ABSTRACT

A method or computer program for forming a digital model of a patient's teeth. The method includes the steps of: obtaining a plurality of projection images acquired by scanning a negative impression of the patient's teeth using a computed tomographic imaging apparatus; generating, from the plurality of projection images, an air volume model of the air that surrounds the negative impression; defining a (Continued)

transition surface along edges of the air volume model that touch the negative impression; forming the digital model of the patient's teeth according to the defined transition surface; and displaying, storing, or transmitting at least a portion of the digital model of the teeth.

13 Claims, 8 Drawing Sheets (51) Int. Cl.
    *G06T 7/00* (2017.01)
    *G06T 7/11* (2017.01)
    *G06T 7/136* (2017.01)
    *A61C 9/00* (2006.01)
    *G06K 9/46* (2006.01)
    *A61C 7/00* (2006.01)
    *A61B 6/14* (2006.01)

(52) U.S. Cl.
    CPC .............. *G06T 7/11* (2017.01); *G06T 7/136* (2017.01); *G06T 11/003* (2013.01); *G06T 11/008* (2013.01); *G06T 17/00* (2013.01); *A61B 6/14* (2013.01); *A61C 7/002* (2013.01); *A61C 9/004* (2013.01); *G06T 2207/10072* (2013.01); *G06T 2207/10081* (2013.01); *G06T 2207/20024* (2013.01); *G06T 2207/30036* (2013.01); *G06T 2210/41* (2013.01)

(56) References Cited

U.S. PATENT DOCUMENTS

| | | | | |
|---|---|---|---|---|
| 6,532,299 | B1* | 3/2003 | Sachdeva | A61C 7/00 382/128 |
| 6,767,208 | B2* | 7/2004 | Kaza | A61C 7/002 433/24 |
| 7,068,825 | B2* | 6/2006 | Rubbert | A61C 7/00 382/128 |
| 7,140,877 | B2 | 11/2006 | Kaza | |
| 7,905,725 | B2* | 3/2011 | Chishti | A61C 7/00 433/24 |
| 8,573,972 | B2* | 11/2013 | Matov | A61C 7/08 433/196 |
| 8,821,158 | B1* | 9/2014 | Hultgren | A61C 9/0006 433/215 |
| 2003/0235265 | A1* | 12/2003 | Clinthorne | A61B 6/14 378/4 |
| 2004/0214128 | A1* | 10/2004 | Sachdeva | A61C 7/00 433/24 |
| 2007/0218426 | A1* | 9/2007 | Quadling | A61C 13/0004 433/223 |
| 2008/0020350 | A1* | 1/2008 | Matov | G06T 17/20 433/213 |
| 2008/0084965 | A1* | 4/2008 | Ohnona | A61B 6/14 378/98 |
| 2009/0220916 | A1* | 9/2009 | Fisker | A61C 9/00 433/201.1 |
| 2010/0106275 | A1* | 4/2010 | Andersson | A61C 9/0006 700/98 |
| 2010/0219546 | A1* | 9/2010 | Puttler | A61C 7/00 264/16 |
| 2012/0329008 | A1* | 12/2012 | Fishman | A61C 13/0004 433/172 |
| 2013/0022255 | A1* | 1/2013 | Chen | G06K 9/34 382/131 |
| 2013/0089246 | A1* | 4/2013 | Souza | G06T 5/002 382/128 |
| 2016/0000525 | A1* | 1/2016 | Inglese | A61C 7/002 433/214 |

FOREIGN PATENT DOCUMENTS

| | | |
|---|---|---|
| EP | 2 674 106 A2 | 12/2013 |
| WO | WO 2009/042378 | 4/2009 |

OTHER PUBLICATIONS

G.R.J.Swennen, et al., "A cone-beam CT based technique to augment the 3D virtual skull model with a detailed dental surface," Int. J. Oral Maxillofac. Surg., 2009, 38, pp. 48-57.

Joost M. Verburg, et al., "CT metal artifact reduction method correcting for beam hardening and massing projections," Physics in Medine and Biology, 57, 2012, pp. 2803-2818.

* cited by examiner

METHOD FOR PRODUCING TEETH SURFACE FROM X-RAY SCAN OF A NEGATIVE IMPRESSION

CROSS REFERENCE TO RELATED APPLICATIONS

This application claims the benefit of and is a U.S. National Phase filing of PCT Application PCT/US2014/022345 filed Mar. 10, 2014 entitled "METHOD FOR PRODUCING TEETH SURFACE FROM X-RAY SCAN OF A NEGATIVE IMPRESSION", in the name of Maury et al, which claims the benefit of (i) U.S. Provisional Patent Application No. 61/775,942 provisionally filed on Mar. 11, 2013, entitled "METHOD FOR PRODUCING TEETH SURFACE FROM X-RAY SCAN OF A NEGATIVE IMPRESSION", in the names of Maury et al. and (ii) U.S. Provisional Patent Application No. 61/775,949 provisionally filed Mar. 11, 2013, entitled "METHOD FOR PRODUCING TEETH SURFACE FROM X-RAY SCAN OF A NEGATIVE IMPRESSION", in the names of Maury et al., all of which are incorporated herein in their entirety.

TECHNICAL FIELD

The disclosure is related generally to the field of dental imaging and dental care and more particularly to methods for forming volume images of dental features.

BACKGROUND OF THE INVENTION

Orthodontics focuses on diagnosis, planning, and treatment of various types of dental and skeletal malocclusions, for the purpose of improving the position and movement of the teeth. Orthodontic procedures, for example, readjust the position of teeth so that the teeth function optimally and are more aesthetically pleasing. Various types of appliances such as braces and wires can be positioned on a patient's teeth by a practitioner such as an orthodontist or a suitably trained dentist. Once mounted on the teeth, the hardware exerts continual forces on the teeth and gradually urges the teeth toward their ideal positions. Over a period of time, the practitioner adjusts the braces and the wires to urge the teeth toward their final destination.

Dental study casts are widely used in orthodontics and related disciplines and help to provide improved understanding of how a patient's teeth and bite function. The study of the static relationship of teeth and bite that is provided serves a number of functions, including a diagnostic function for interpretation of discrepancies or problems related to the bite relationship. The study casts further improve communication as a concrete model, helping the practitioner and patient to better understand discrepancies in tooth function. The dental study cast also helps to more precisely define pre-existing static bite relationships prior to the performance of any corrective work.

The plaster cast is formed using a series of impressions taken to obtain the geometry of the teeth. To take an impression, alginate or other impression material is poured into a tray (i.e., an impression tray) which is then introduced into the patient's mouth for a period of time (typically one to two minutes). The impression material sets about the teeth and soft tissues forming a negative impression. The patient also bites into a soft material for registering a simultaneous imprint of the upper and lower teeth which records the relationship of the teeth in the upper and lower jaws respectively in three planes of space. Once the impressions have set, they are sent to a lab to be processed into an upper and/or lower plaster study cast. The study casts are articulated together via the bite registration material to reproduce the bite of the patient. After construction, the study casts are returned to the dentist/orthodontist as a working study cast.

One aspect of conventional preparation methods relates to the number of labor intensive steps to produce the study casts, the space and storage of the study casts, and the inability to interface the study casts interactively with other diagnosis information (e.g., photographs and radiographs). In some cases, if additional work is required, or if the cast fails in some way or is damaged or lost, an additional impression series is taken. Therefore, there also exists a need in the art to develop a set of electronic data from the series of dental impressions wherein only a single impression need be taken for multiple interactive functions.

In a conventional sequence for orthodontic planning, the cast that represents the patient's teeth can then be scanned, such as using laser scanning or using a computed tomography (CT) or a cone-beam computed tomography (CBCT) scanning apparatus. The scanned data then provides baseline information as a reference for subsequent adjustments to tooth positioning that will be made over time. The process for obtaining this data requires several of the same steps used for conventional cast preparation. First, a negative impression is made of the patient's teeth, such as impression formed using an alginate material and provided in a tray. Next, the impression is used as a mold for casting the positive mold or model of the patient's dentition. The positive mold is then scanned using laser scanning or CBCT to form a volume image. The volume image that is generated in this way can then be used on a 3-D visualization system for modeling adjustments to be made to tooth position and angle. General techniques for producing plaster casts of teeth and generating digital models using laser scanning techniques are described, for example, in U.S. Pat. No. 5,605,459 (Kuroda).

Among drawbacks of the conventional method is the formation of a plaster mold to serve as an intermediate for the CBCT scan. Preparing the mold is a labor-intensive manual process, takes time, and, even when performed by a skilled technician, can suffer from some inaccuracy and dimensional distortion. The plaster model that is made is fragile and subject to damage.

For conventional approaches to providing a model of teeth in the upper and/or lower jaw of a patient, reference is made to WO2009/042378 (Puffier) and to U.S. Pat. No. 8,573,972 (Matov). Reference is also made to U.S. Pat. No. 7,140,877 (Kaza) and U.S. Pat. No. 6,767,208 (Kaza). Scanning of the mouth or an impression using optical systems is described, for example, in U.S. Pat. No. 7,905,725 (Chisti). Scanning using a hand-held scanning device is described in U.S. Pat. No. 7,068,825 (Rubbert). Laser scanning is described in U.S. Pat. No. 6,217,334 (Hultgren). Reference is also made to EP 1119312(B1) (Jones), CA 2346256(A1) (Chishti), and U.S. Pat. No. 6,532,299 (Sachdeva).

While these disclosures may help to provide some level of volume imaging information from scans of the mouth or of dental impressions/plaster casts, there is still room for improvement.

There is a need for methods that simplify the generation and use of models of tooth surfaces for orthodontic planning.

SUMMARY

Embodiments of the present disclosure are directed to improved methods for generating a model of the tooth surfaces. The present disclosure provides a method to create a digital model of a patient's teeth that includes accessing and/or creating an impression of the patient's teeth; and scanning the impression using an X-ray source to generate the digital model.

Advantages of the invention may include eliminating the fabrication of the plaster models of a patient's dentition in some cases. The capability for digital manipulation, digital detailing based on iterative processing, and image correction help to improve overall accuracy of results. The same system used to scan plaster models can be used to scan impressions directly, providing useful data for patient treatment.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According with at least one aspect of the disclosure there is provided a method or computer program for forming a digital model of a patient's teeth, comprising the steps of: obtaining a plurality of projection images acquired by scanning a negative impression of the patient's teeth using a computed tomographic imaging apparatus; generating, from the plurality of projection images, an air volume model of the air that surrounds the negative impression; defining a transition surface along edges of the air volume model that touch the negative impression; forming the digital model of the patient's teeth according to the defined transition surface; and displaying at least a portion of the digital model of the teeth.

According to another aspect of the disclosure, there is provided a method or computer program for forming a digital model of a patient's teeth, comprising: obtaining a plurality of projection images acquired by scanning a negative impression of the patient's teeth using a computed tomographic imaging apparatus; generating, from the plurality of projection images, an air volume model of the air that surrounds the negative impression; refining the projection images or the air volume model to reduce at least beam hardening artifacts or noise; defining a transition surface along edges of the air volume model that touch the negative impression; forming the digital model of the patient's teeth according to the defined transition surface; and displaying at least a portion of the digital model of the teeth.

According to yet another aspect of the disclosure, there is provided a method or computer program for forming a digital model of a patient's teeth, comprising: obtaining a plurality of projection images acquired by scanning a negative impression of the patient's teeth using a computed tomographic imaging apparatus; iteratively generating an air volume model by: (i) forming a volume image from the projection images; (ii) applying a binary filtering to the volume image and generating a plurality of filtered images according to the binary filtering; (iii) forming a first volume reconstruction of the air volume according to the generated plurality of filtered images; (iv) reducing beam hardening artifacts in the volume reconstruction of the air volume according to path length detection from the binary filtered images; defining a transition surface according to the volume reconstruction of the air volume, wherein the transition surface lies along edges of the air volume model; forming the digital model of the patient's teeth according to the defined transition surface; and displaying at least a portion of the digital model of the teeth.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

This application claims priority to U.S. Ser. No. 61/775,942, provisionally filed on Mar. 11, 2013 entitled "METHOD FOR PRODUCING TEETH SURFACE FROM X-RAY SCAN OF A NEGATIVE IMPRESSION" and claims priority to U.S. Ser. No. 61/775,949, provisionally filed on Mar. 11, 2013 entitled "METHOD FOR PRODUCING TEETH SURFACE FROM X-RAY SCAN OF A NEGATIVE IMPRESSION", both in the names of Bothorel et al., and both incorporated herein by reference in their entirety.

The following is a detailed description of the preferred embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

In the context of the present disclosure, the term "volume image" is synonymous with the terms "3-Dimensional image" or "3-D image". An image slice or "2-D slice" is a 2-D image that has been extracted from the full 3-D volume.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D projection images of pixels, taken at different relative angles, then combining the projection image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

In the context of the present disclosure, the terms "viewer", "operator", "viewing practitioner", "observer", and "user" are considered to be equivalent and refer to the viewing practitioner or other person who views and manipulates a radiographic image on a display monitor or other viewing apparatus. Viewer preferences relate to the particular viewer who observes a displayed image or image slice.

CT and CBCT imaging utilize 2-D radiographic data in order to form a 3-D image volume. In this type of imaging, the same voxel (that is, the same point in space) is measured multiple times. For example, a first radiation beam is directed through the voxel at a first angle and a portion of this radiation, proportional to the density of the material, passes through the voxel and forms an image on the detector. This process then repeats at a second angle, a third angle, and so on. The capability to obtain radiodensity information of a voxel from multiple angles allows information about the material content of the voxel to be deduced. An attenuation coefficient μ can be determined or approximated for the voxel, in terms of CT numbers, in terms of relative or actual Hounsfield units, or on some other appropriate scale. The attenuation coefficient or corresponding attenuation data can then be used to yield information about the type of tissue or composition of material that is being measured. The applicants have developed techniques for developing and refining relative attenuation information for voxels from the CT or CBCT scan data and for using this information for obtaining accurate information related to the tooth surfaces, without requiring a direct scan of the patient anatomy and without requiring that a plaster cast be formed from an impression obtained from the patient's mouth.

Figure 1:
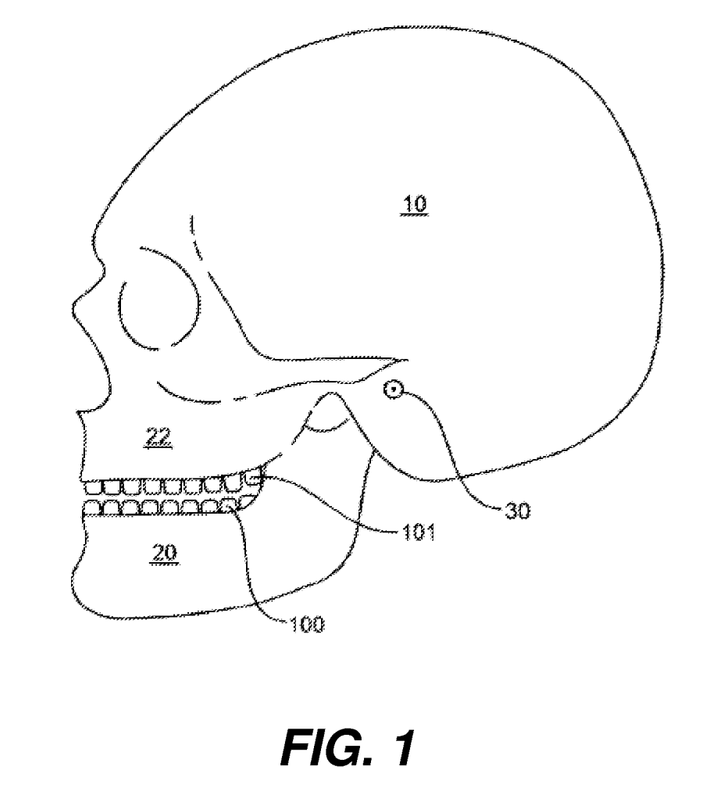
FIG. 1 is a side view showing features of the human skull.

FIG. 1 shows a human skull 10 with an upper jaw bone 22 and a lower jaw bone 20. The lower jaw bone 20 hinges at a joint 30 to the skull 10. The upper jaw bone 22 is associated with an upper jaw 101, while the lower jaw bone 20 is associated with a lower jaw 100.

For orthodontics work, a computer model of the jaws 100 and 101 can be generated, and a computer simulation model can be used to show interactions between the teeth on the jaws 100 and 101. The computer simulation allows the system to focus on motions and interaction involving contacts between teeth mounted on the jaws 100, 101. The computer simulation allows the system to render realistic jaw movements which are physically correct when the jaws 100 and 101 contact each other. For example, the model of the jaw can show the current condition of teeth and can also place the individual teeth in a treated position, which may be of interest in orthodontics. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions can be applied to one jaw, or may be applied to both jaws.

A scanner can be employed to scan an impression model (either a positive impression or a negative impression) of the patient's teeth. Such an impression can be obtained either from the patient or from another dental practitioner such as an orthodontist. The scanned digital data set information is provided to a data processing system for further processing. In a distributed processing environment, the scanner may be located at a remote location and communicate scanned digital data set information to data processing system over a network interface.

Figure 2:
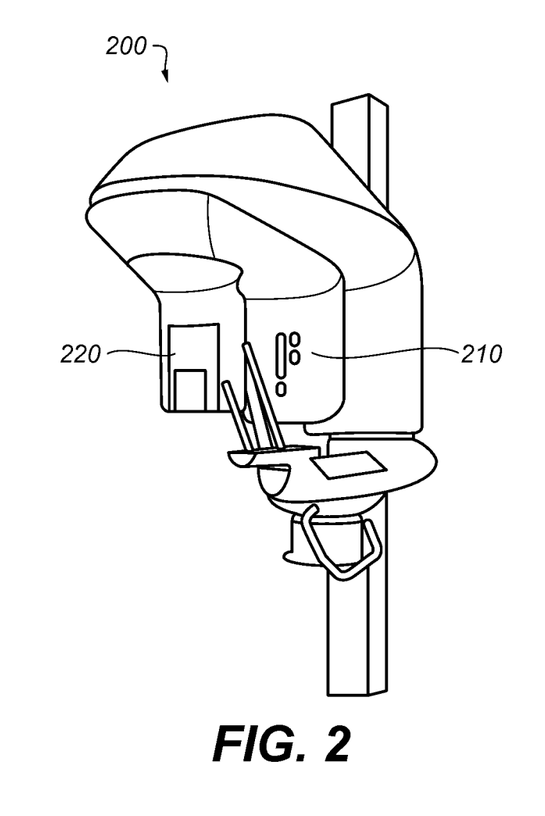
FIG. 2 shows a perspective view of a CT scanner.

The scanner can be an x-ray scanner. An example of an x-ray scanner is a Computed Tomography (CT) system, which utilizes fan-beam CT or cone-beam CT (CBCT) techniques, well-known in the diagnostic imaging arts. FIG. 2 shows an example of a CT scanner 200 used for dental imaging. CT scanner 200 has an x-ray source 210 and a detector 220 that orbit the patient for obtaining multiple 2-D projection images that are used to generate a volume image. In a preferred arrangement, a CBCT system is used.

Figure 3:
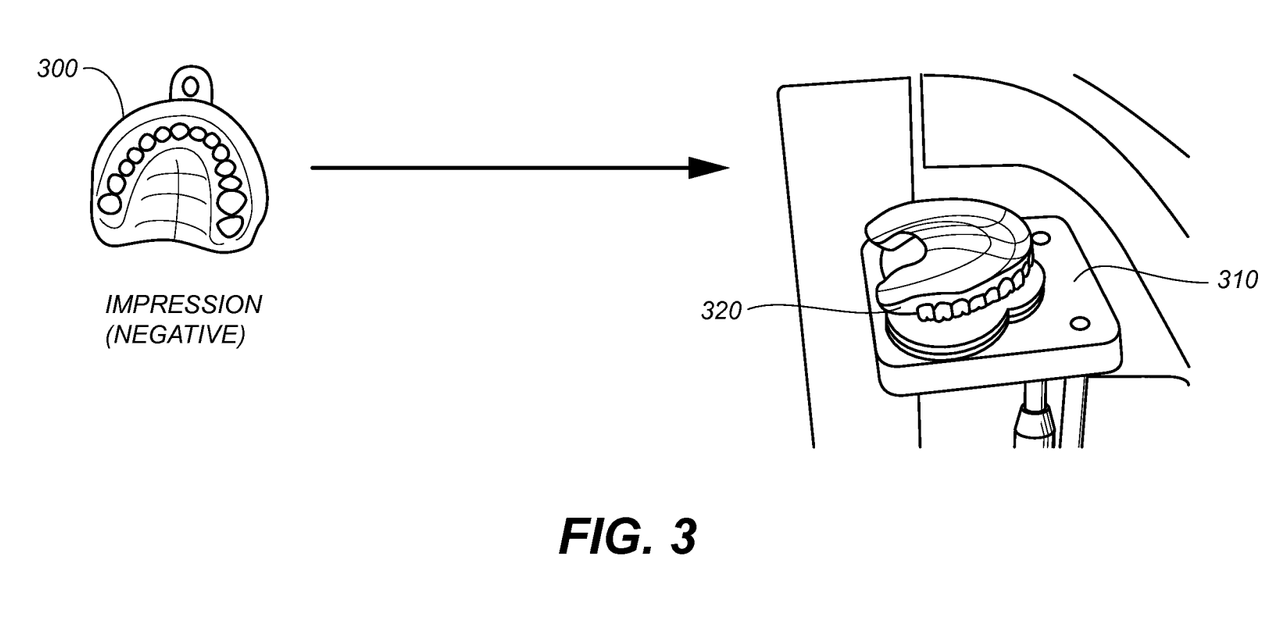
FIG. 3 shows an impression for forming a plaster model that can be scanned using CT scanner.

FIG. 3 shows use of an impression 300 for forming a plaster model 320 that can be scanned using CT scanner 200. Embodiments of the present disclosure can scan impression 300 directly for obtaining a digital model of the patient's teeth. Alternately, CT scanner 200 can be used to scan plaster model 320 or both impression 300 and plaster model 320.

Figure 4:
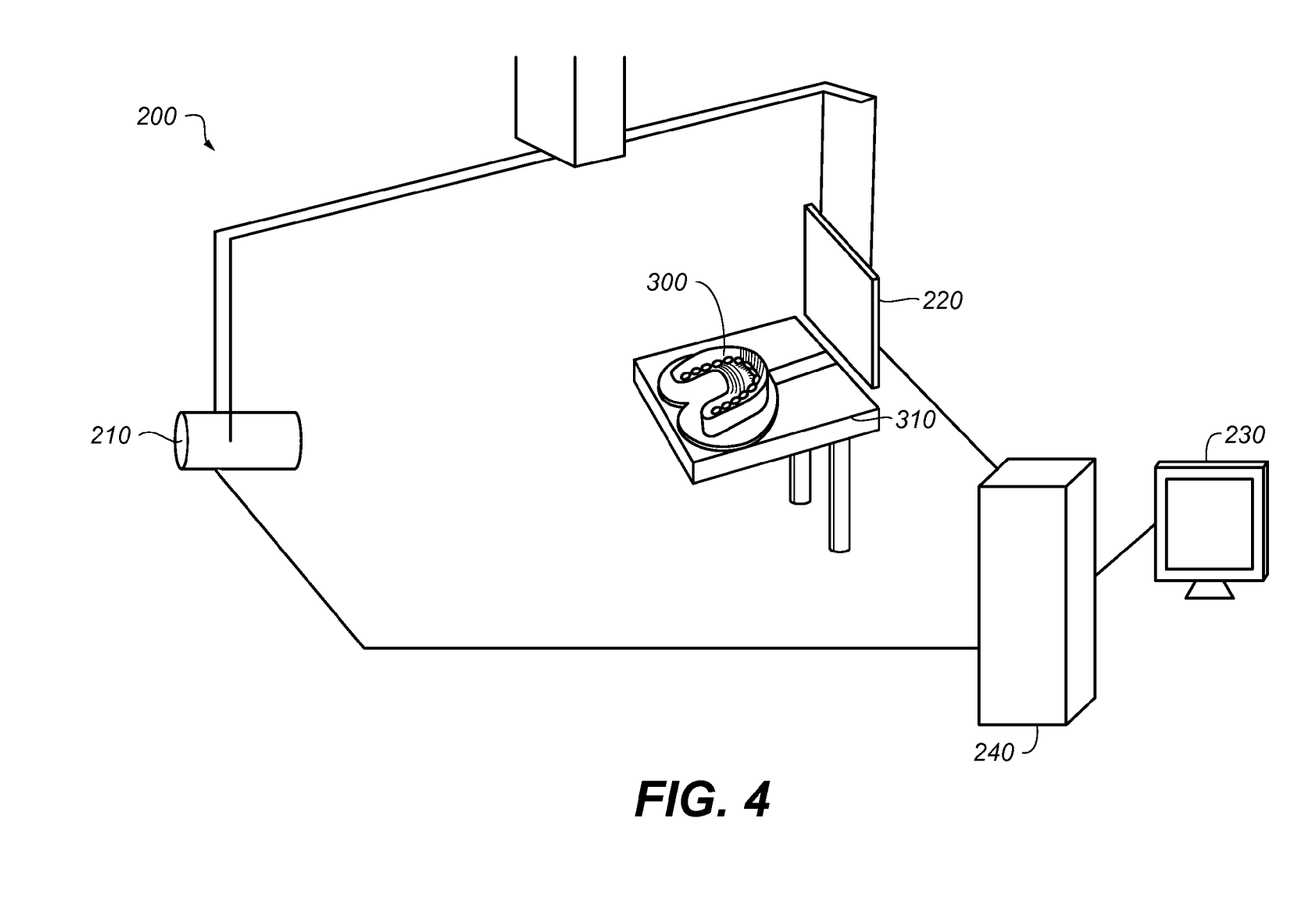
FIG. 4 shows a system for forming an image of teeth by scanning a negative impression.

Referring to FIG. 4, an impression 300 to be scanned is placed on a table or other type of support 310. The impression 300 is irradiated by an x-ray beam emitted by x-ray source of the CT system. As is well known in the art for CT systems, radiation is swept through the impression 300 and captured for measurement by x-ray digital detector 220. The detector 220 provides the information to a computer/processor 240 for processing and displaying an image on a display 230 that is in signal communication with processor 240. Impression 300 can be a wax bite or other type of impression material. The upper, lower, and bite impressions can be scanned using a CBCT system to generate digital scanned data. The upper and lower bite impressions can be scanned together, separately, or in various combinations.

In one arrangement, the negative impression of each of the upper and lower jaw is scanned as impression 300. In addition, the wax bite (or other bite material, such as silicon) can also be scanned. The scanning of these three items or of other materials used to form impression 300 can be accomplished individually or in various combinations, along with scans obtained from a plaster cast of at least a portion of the upper and/or lower jaw.

Using the negative impression of the patient's teeth for the CT system's scan eliminates the need to create a positive plaster model for each jaw. When using this method, software on computer 240 acquires the scan data and then automatically generates a digital positive model of the patient's teeth from the scan data of the negative impression. The generation uses software techniques employed for cone beam reconstruction, with processing adapted to more accurately indicate the location of teeth and related structures using information obtained from the negative impression. Using this technique, a digital model of the upper and lower jaw can then be put together using the information from the scan data of a wax bite or other impression, without directing radiation to the patient and without the effort, time, and expense of forming a plaster positive.

Figure 5:
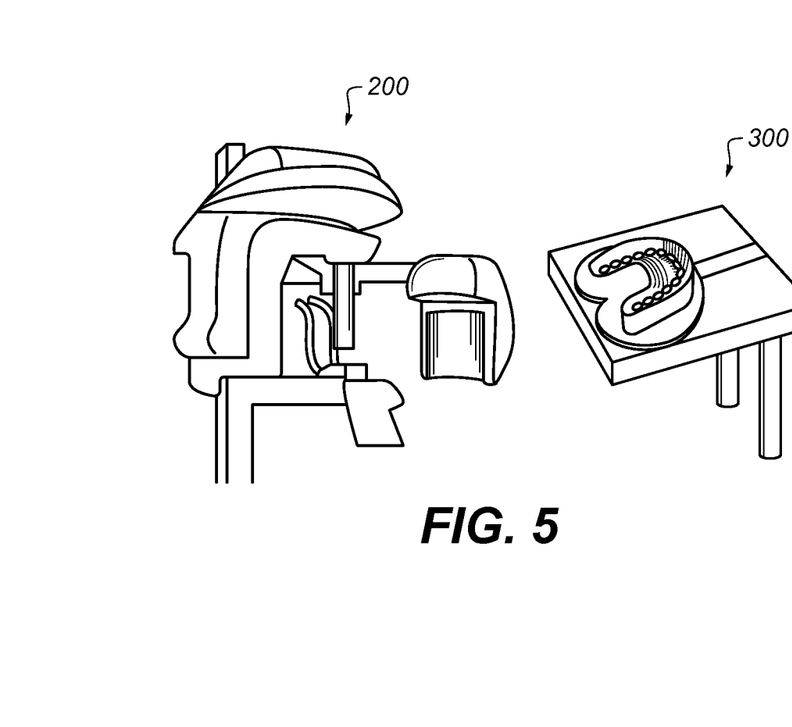
FIG. 5 shows a CT scanner that can be used to acquire data from an impression.
Figure 6:
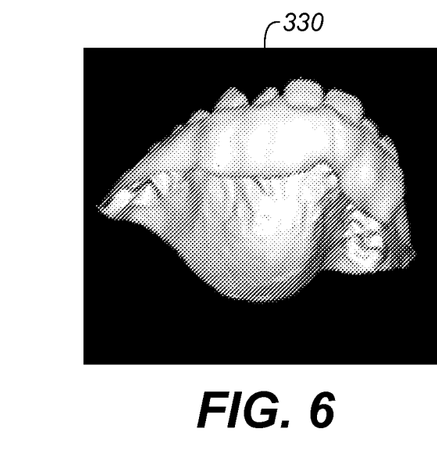
FIG. 6 shows a computer-generated model that can be formed without the need to form a plaster model, using an embodiment of the present disclosure.

FIG. 5 shows a CT scanner 200 that can be used to acquire scan data either from a patient or from an impression 300. FIG. 6 shows a computer-generated positive model 330 that can be formed without the need to form a plaster model, using an embodiment of the present disclosure.

Figure 7:
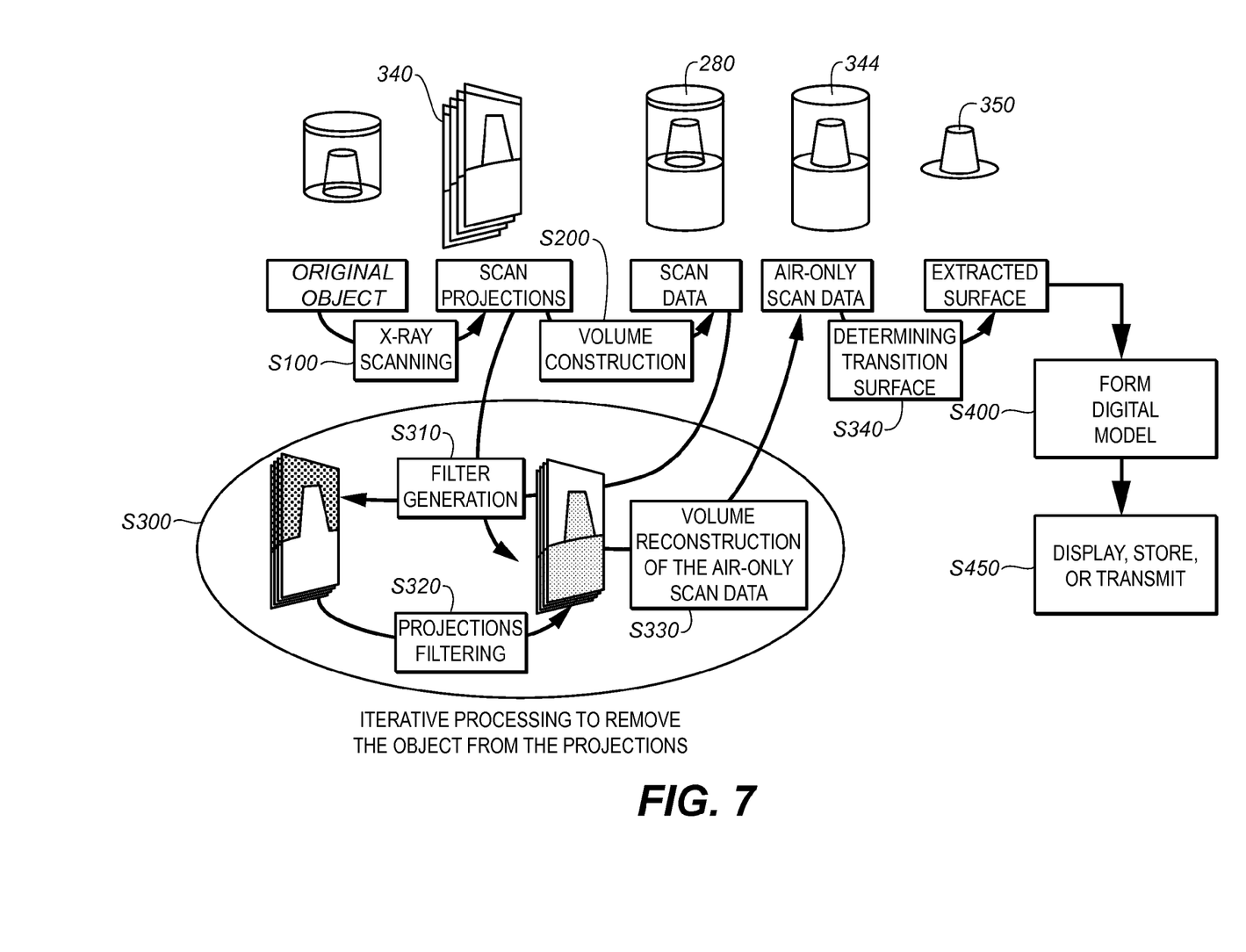
FIG. 7 is a flow diagram showing an overall sequence that can be used for generating a model of the tooth surface from a negative impression according to an embodiment of the present disclosure.

FIG. 7 shows an overall sequence of steps that can be used for generating a digital model of the tooth surface from scanning a negative impression. In an acquisition step S100, impression 300 (see FIG. 4) is obtained from the patient and scanned to obtain projection images 340. A volume reconstruction step S200 then forms a volume image 280 from the projection images 340. The volume image 280 from step S200 is then processed in an iterative processing step S300 in order to obtain air-only scan data 344. This process uses the volume reconstruction of volume image 280 to generate mask information in a filter generation step S310. The mask that is generated provides initial definition of air and non-air voxels. Mask generation from volume image data is a procedure known to those skilled in the image processing arts and can be executed using thresholding or other techniques. A processing step S320 processes and refines the generated mask information to generate projection pixel information that can be used for volume reconstruction of air-only data that surrounds and is bounded by the impression. Processing step S320 applies various rules for resolving data ambiguity and noise reduction, such as rules for checking connectedness and discontinuity. This is followed by generating a second volume reconstruction using the mask data in a reconstruction step S330. One or more iterations of steps S310, S320, and S330 then validate the mask information and attempt to resolve ambiguities for voxels at air-material transitions and to correct and remove discontinuities in surface profile data. The second volume that has been generated as a result of steps S310, S320, and S330, providing air-only scan data 344, is then processed in a surface detection step S340 in order to determine a transition surface 350 that defines the surface of the teeth and adjacent structures. Transition surface 350 is the surface that is defined where the air volume is bounded by the impression material; alternately, transition surface 350 can be considered as the outer surface of the impression material.

Iterative processing step S300 shown in FIG. 7 includes using prior knowledge to correct the volume information. Iterative processing may also include noise reduction processing using well-known techniques. Noise can be corrected in projection images at the pixel level, then the volume can be re-projected using adjusted projections to correct the original projection image data prior to conducting another reconstruction. This additional reconstruction with adjustment to projection images may be executed two or more times.

Transition surface 350 data can then be further refined in order to generate a computer model of the teeth in a model forming step S400. Step S400 forms the digital model for teeth in the upper or lower jaw of the patient according to the defined transition surface. One or more slices/aspects/portions of the digital model can then be displayed, stored, or transmitted in step S450.

The generated computer model is then available to the practitioner for viewing from multiple slice angles, for treatment planning, and for comparison with later imaging and with the patient's mouth as treatment of the patient proceeds. The process can be repeated for upper and lower jaws. Once the upper and lower digital models are generated, they can be aligned into a bite position using bite digital scan data.

Figure 8:
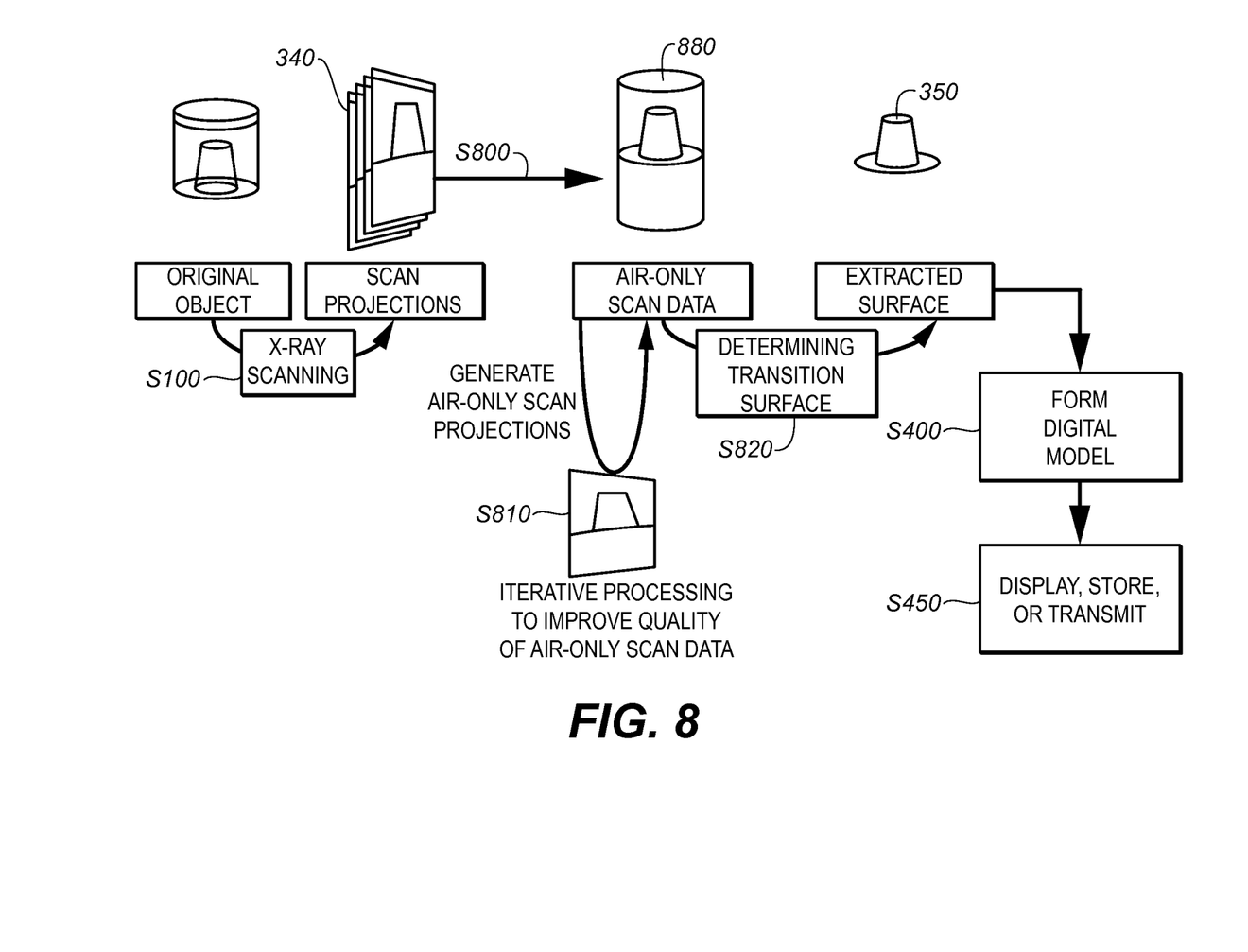
FIG. 8 is a flow diagram showing an overall sequence that can be used for generating a model of the tooth surface from a negative impression, according to an alternate embodiment of the present disclosure.

The flow diagram of FIG. 8 shows an overall sequence that can be used for generating a model of the tooth surface from a negative impression according to an alternate embodiment of the present disclosure. In acquisition step S100, impression 300 (see FIG. 4) is obtained from the patient and scanned to obtain projection images 340. A volume reconstruction step S800 then forms a volume image 880 from the projection images 340, using conventional techniques, such as FBP or FDK projection. The full volume is not reconstructed from projection images 340; only the air-only scan data is reconstructed. During the reconstruction process, every time a voxel value is calculated, if it is identified as an object value, the value is set to 0, else if it is identified as air value it is not modified, thus ensuring the air-only reconstruction; the identification of a voxel value as air or object is done using a threshold. Iterative processing S810 is performed to improve the quality of the air-only reconstruction. A surface detection step S820 then executes to determine the transition surface of the teeth and generate transition surface 350. Procedures for iterative processing S810 to remove the object from the projections (illustrated in FIG. 8), include: filter generation, projections filtering, and volume reconstruction of the air-only volume data. Procedures repeats minimizing a cost function based on the noise. At each iteration, the computed air-only volume contains less noise and, therefore, a better contrast-to-noise ratio. This is done until the target image quality is achieved, for instance when the noise becomes lower than a threshold.

As is well known to those skilled in the volume image reconstruction arts, artifacts are prone to occur because of beam hardening that occurs with polychromatic or polyenergetic radiation. Caused by the preferential attenuation of low-energy photons in a polyenergetic beam, beam hardening happens when a material that is highly dense absorbs lower energy (lower frequency) radiation so that the remainder of the beam contains higher energy. Beam hardening artifacts vary according to the shape of the scanned object. Unless it is corrected, beam hardening causes low-frequency artifacts that appear as pronounced bright and dark shadows that originate at, and extend outward from, the interface surfaces.

Classical backprojection techniques, such as conventional Feldkamp-Davis-Kress (FDK) reconstruction, assume a linear relationship between object density and object length, as described by the Beer-Lambert law, familiar to those skilled in the volume reconstruction arts. However, in practice, the Beer-Lambert law is not satisfied, due to spectral differences in absorption. Beam hardening results so that the reconstructed density of air at the vicinity of the object is reconstructed with errors and uncertainty in the delineation of the reconstructed air data envelope.

Embodiments of the present invention correct for beam hardening and other effects using an iterative filtering technique that compensates for the polyenergetic contribution of the scan radiation, so that reconstruction uses data that more closely approximates the more accurate data that would be obtained from monochromatic radiation. With this technique, beam hardening effects are successively removed so that the air volume that is generated is relatively free of artifacts. This technique makes use of the artifact reduction techniques described by Joost M. Verburg and Joao Seco entitled "CT metal artifact reduction method correcting for beam hardening and missing projections" in Physics in Medicine and Biology, 57 (2012) pp. 2803-2818 which is hereby incorporated by reference.

Figure 9:
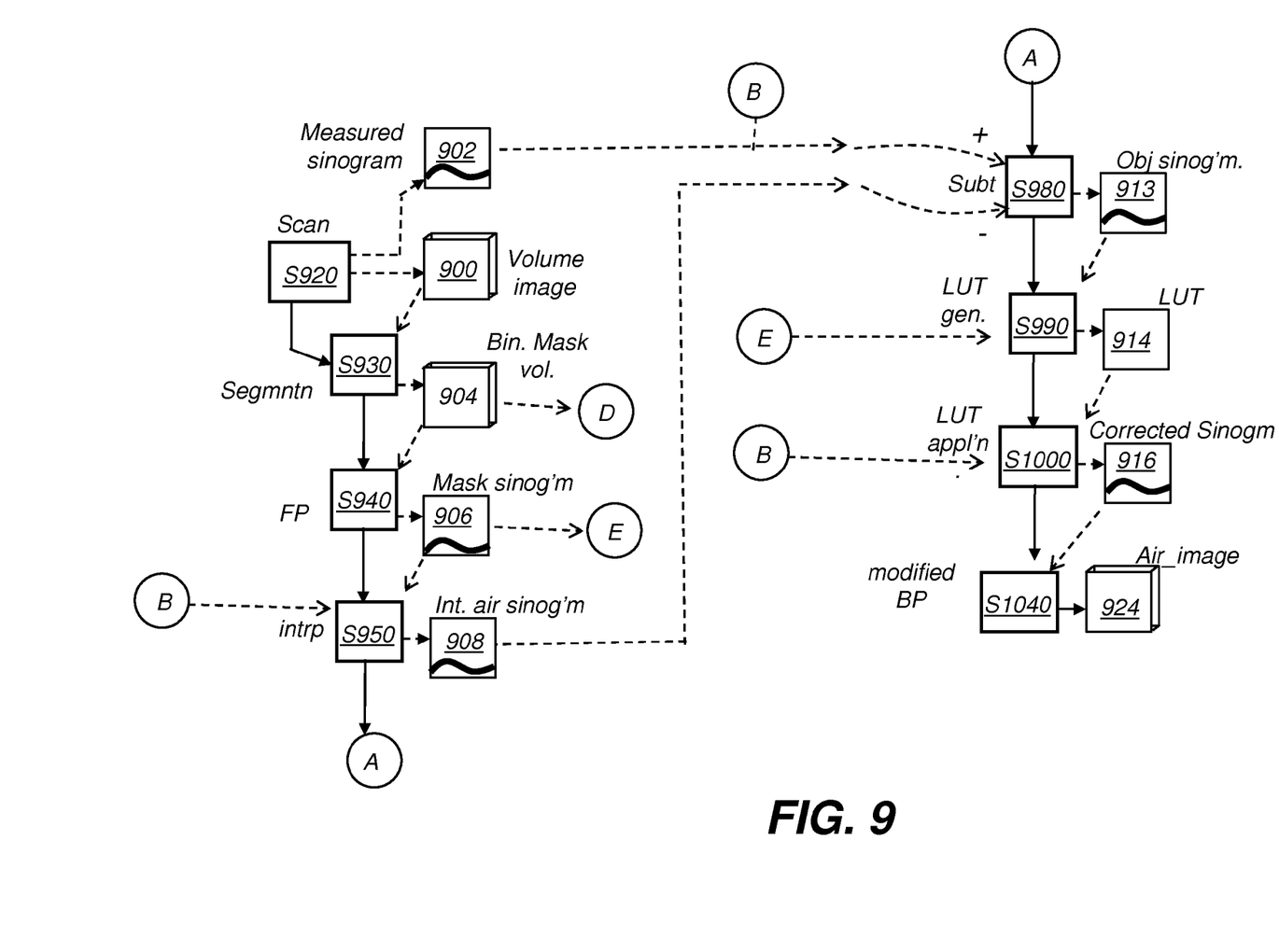
FIG. 9 is a flow diagram showing the steps for generating an air image used for forming a model of the patient's teeth, according to an embodiment of the present disclosure.

The logic flow diagram of FIG. 9 shows a sequence of steps for generating the air-only volume data or air volume model according to an embodiment of the present disclosure. An impression is prepared as the object for scanning and placed in the CBCT scanner, as described previously in a scan step S920, multiple projection images are obtained: these projections images are named scan projections (340 in FIG. 7) or measured sinogram (902 in FIG. 9). A back projection technique such as FDK or FBP generates a volume image: 280 in FIG. 7, 900 in FIG. 9.

A volume segmentation step S930 then segments the volume into two classes: object (impression material) and air. Binarization is applied to the results of step S930, generating a binary mask volume 904. As the term implies, the binary mask volume 904 has voxels in either of two classes. For example, air voxels have a value of 0; impression material voxels have a value of 1. The segmentation method that is used can apply any of a number of known routines for segmentation, such as thresholding, for example. The segmentation method can be specified so that it reduces or minimizes the standard deviation for the two classes. Although forming a binary mask can be a formidable processing task when processing live tissue or other variegated objects, the problem with a scanned impression is simpler. Two materials having very different densities are of interest: air and impression material (generally wax or plastic).

A forward projection step S940 then forward projects the binary mask volume to obtain a mask sinogram 906. To perform a forward projection, we simulate the trajectory of the x-ray from the source to the sensor through the mask volume, one ray producing one sinogram pixel. Mask sinogram 906 is conditioned by the length of the object that is seen by each ray. Using mask sinogram 906, the length of each ray through the object (the impression) can be determined. The mask sinogram allows identification of each ray that encounters the impression and allows replacement of values in the measured sinogram 902 with interpolated values for generation of an interpolated air sinogram 908 in an interpolation step S950. The interpolation can be, for example, a linear interpolation between identified air zones in the measured sinogram 902.

A subtraction step S980 then subtracts air sinogram 912 from measured sinogram 902 to obtain an object sinogram 913.

A Look-Up Table (LUT) generation step S990 then uses mask sinogram 906 and object sinogram 913 to relate measured sinogram values to the length of the object (impression) seen by each ray. To do this, comparison is made, for each pixel, between each of sinograms 906 and 913, and a mapping generated according to the relative length of the object that is seen by each corresponding ray. This mapping can be stored as a LUT 914 or in some other form.

A LUT application step S1000 applies LUT 914 to mask sinogram 906 to generate a polychromatic object sinogram 916.

A reconstruction step S1040 reconstructs air scan data to form a volume air image 924. Only the air scan data is reconstructed. During the reconstruction process, every time a voxel value is calculated, if it is identified as an object value, the value is set to 0, else if it is identified as air value it is not modified, thus ensuring the air-only reconstruction; the identification of a voxel value as air or object is done using a threshold. The transition surface at the air-impression interface can then be determined and used to provide a model of the patient's jaw, as described with reference to step S340 in FIG. 7.

Additional steps can be executed by the operator following reconstruction and display of the patient's teeth from the scanned impression. These include digital detailing, which gives the operator the opportunity to perform some level of interactive cleanup on the volume reconstruction. For example, there may be one or more regions outside the tooth area that are visible as the image displays and can be removed by the operator using cleanup functions.

CT scanner 200 (FIG. 2) can also be used to scan a plaster cast formed using conventional methods. Results from the scan of the plaster cast can be used along with results from a scanned impression as described herein. In addition, it may be useful to form and scan a plaster cast for one of the jaws, such as the lower jaw, while only scanning the negative impression for the other jaw, such as the upper jaw. Using embodiments of the present disclosure, equivalent information can be obtained from either scanning the positive plaster cast or the negative impression.

According to an embodiment of the present disclosure, there is provided a method to create a digital model of a patient's teeth, comprising: accessing a negative impression of the patient's teeth; using a CBCT system, scanning the impression of the patient's teeth to generate scan data; and automatically generating a positive digital model of a portion of the patient's teeth using the generated scan data, the generating being accomplished without digitally reversing the scan data. There is further provided a method to create a digital model of a patient's teeth, comprising: accessing a negative impression of the patient's teeth; using a CBCT system, scanning the impression of the patient's teeth to generate scan data; and automatically generating a positive digital model of a portion of the patient's teeth using the generated scan data, the generating being accomplished without digitally reversing the scan data. This method can be executed with an impression creating using a tray. There is further provided a method to create a digital model of a patient's teeth, comprising: accessing a negative impression of the patient's teeth; using a CBCT system, scanning the impression of the patient's teeth to generate scan data comprising an image of at least a portion of the negative impression; and automatically generating a positive digital model of a portion of the patient's teeth using the generated scan data, the generating being accomplished without digitally reversing the scan data.

Consistent with an embodiment of the present invention, a computer program utilizes stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for forming a digital 3D surface model of a patient's teeth, comprising:
    obtaining a plurality of projection images acquired by scanning a physical model of the patient's teeth or at least one of the patient's teeth using a computed tomographic x-ray 3D volume imaging apparatus;
    generating, from the plurality of projection images, an air 3D volume model of the air that surrounds the physical model or the at least one of the patient's teeth;
    defining a transition surface along edges of only the air 3D volume model that touch the physical model or the at least one of the patient's teeth;
    forming the digital 3D surface model of the patient's teeth according to the defined transition surface of the air volume model; and
    displaying, storing, or transmitting at least a portion of the digital model of the teeth.

2. The method of claim 1 wherein obtaining the plurality of projection images comprises obtaining images from a cone-beam computed tomography apparatus.

3. The method of claim 1 wherein generating the plurality of projection images of the air 3D volume model further comprises forming a binary mask volume representative of the air 3D volume and of the physical model.

4. The method of claim 3 wherein generating the binary mask volume model further comprises forward projecting the binary mask volume to form a mask sinogram and combining the mask sinogram with a measured sinogram obtained from the obtained plurality of projection images.

5. The method of claim 1 wherein a final volume is generated so as to produce only the air 3D volume model.

6. The method of claim 1 further comprising obtaining the physical model using a tray or a wax bite.

7. The method of claim 1 further comprising refining the projection images or the air 3D volume model by reducing noise.

8. The method of claim 1 wherein refining the generated air 3D volume model and defining the transition surface are performed iteratively.

9. The method of claim 1 further comprising the step of refining the generated air 3D volume model to reduce at least one artifact.

10. The method of claim 9 wherein the at least one artifact comprises beam hardening or noise.

11. A method for forming a 3D surface digital model of a patient's teeth, comprising:
    obtaining a plurality of projection images acquired by scanning a physical model of the patient's teeth or at least one of the patient's teeth using a computed tomographic x-ray 3D volume imaging apparatus;
    iteratively generating an air volume model by:
        (i) forming a current volume reconstruction image from the plurality of projection images;
        (ii) applying a binary filtering to the current volume reconstruction image and generating a plurality of filtered images representing the air according to the binary filtering; and
        (iii) forming a first volume reconstruction of only the air volume according to the generated plurality of filtered images;
    defining a transition surface according to the first volume reconstruction of only the air volume, wherein the transition surface lies along edges of the first volume reconstruction of only the air volume;
    forming the 3D surface digital model of the patient's teeth according to the defined transition surface; and
    displaying, storing, or transmitting at least a portion of the 3D surface digital model of the teeth.

12. A computer program embodied on a non-transitory computer readable medium for forming a 3D surface digital model of a patient's teeth, the program having instructions such that when executed on a computer will cause the computer to perform the steps of:
    obtaining a plurality of projection images acquired by scanning a physical model of the patient's teeth or at least one of the patient's teeth using a computed tomographic x-ray 3D volume imaging apparatus;
    iteratively generating an air volume model by:
        (i) forming a current volume reconstruction image from the plurality of projection images;
        (ii) applying a binary filtering to the current volume reconstruction image and generating a plurality of filtered images according to the binary filtering; and
        (iii) forming a first volume reconstruction of only the air volume according to the generated plurality of filtered images;
    defining a transition surface according to the first volume reconstruction of only the air volume, wherein the transition surface lies along edges of the first volume reconstruction of only the air volume;

forming the 3D surface digital model of the patient's teeth according to the defined transition surface of the first volume reconstruction of only the air volume; and displaying, storing, or transmitting at least a portion of the 3D surface digital model of the teeth.

13. The method of claim 11, further comprising refining the generated air volume model to reduce at least one artifact, where the at least one artifact comprises beam hardening or noise.

\* \* \* \* \*